(12) United States Patent
Jordan et al.

(10) Patent No.: US 10,458,981 B2
(45) Date of Patent: Oct. 29, 2019

(54) THREE-STEP ACID DISSOCIATION ENZYME LINKED IMMUNOSORBENT (TADELIS) ASSAY

(71) Applicant: Hoffmann-La Roche Inc., Little Falls, NJ (US)

(72) Inventors: Gregor Jordan, Groebenzell (DE); Roland Staack, Munich (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/009,369

(22) Filed: Jun. 15, 2018

(65) Prior Publication Data

US 2019/0011440 A1 Jan. 10, 2019

Related U.S. Application Data

(63) Continuation of application No. PCT/EP2016/080887, filed on Dec. 14, 2016.

(30) Foreign Application Priority Data

Dec. 16, 2015 (EP) ..................................... 15200446

(51) Int. Cl.
| | | |
|---|---|---|
| *G01N 31/00* | (2006.01) | |
| *G01N 33/53* | (2006.01) | |
| *G01N 33/543* | (2006.01) | |
| *G01N 33/536* | (2006.01) | |
| *G01N 33/68* | (2006.01) | |
| *G01N 33/94* | (2006.01) | |
| *G01N 33/58* | (2006.01) | |

(52) U.S. Cl.
CPC ..... *G01N 33/54306* (2013.01); *G01N 33/536* (2013.01); *G01N 33/58* (2013.01); *G01N 33/6854* (2013.01); *G01N 33/94* (2013.01)

(58) Field of Classification Search
None
See application file for complete search history.

(56) References Cited

U.S. PATENT DOCUMENTS

2012/0269728 A1 10/2012 Jen et al.
2015/0226758 A1 8/2015 Grabert et al.

FOREIGN PATENT DOCUMENTS

WO 2015/000865 A1 1/2015

OTHER PUBLICATIONS

Smith et al. Regulatory Toxicology and Pharmacology, vol. 49, pp. 230-237, 2007.*
Li et al. BMC Neuroscience, vol. 8, No. 22, pp. 1-11, 2007.*
Davis et al., "A novel method for quantitative measurement of a biomarker in the presence of a therapeutic monoclonal antibody directed against the biomarker." Journal of Pharmaceutical and Biomedical Analysis 48:897-901 (2008).
Hage et al., "Immunoassays" Anal. Chem. 71:294R-304R (1999).
ISR for PCT/EP2016/080887 (Date of mailing Mar. 27, 2017).
Kelley et al., "Theoretical considerations and practical approaches to address the effect of anti-drug antibody (ADA) on quantification of biotherapeutics in circulation" The AAPS Journal 15:646-58 (2013).
Lee, J.W. et al., "Bioanalytical Approaches to Quantify 'Total' and 'Free' Therapeutic Antibodies and Their Targets: Technical Challenges and PK/PD Applications Over the Course of Drug Development" The AAPS Journal 13:99-110 (2011).
Li et al., "Detection of low-affinity anti-drug antibodies and improved drug tolerance" Journal of Pharmaceutical and Biomedical Analysis 54:286-294 (2011).
Mikulskis et al., "Solution ELISA as a platform of choice for development of robust, drug" Journal of Immunological Methods 365:38-49 (2010).
Moxness et al., "Development and validation of radioligand binding assays to measure total, IgA, IgE, IgG, and IgM insulin antibodies in human serum" Annals of the New York Academy of Sciences 1005:265-268 (2003).
Patton et al., "An acid dissociation bridging ELISA for detection of antibodies directed against therapeutic proteins in the presence of antigen" Journal of Immunological Methods 304:189-195 (2005).
Qiu Z J et al., "A novel hemogeneous Biotin-digoxigenin based assay for the detection of" Journal of Immunological Methods 362:101-111 (2010).
Salimi-Moosavi et al., "Novel approaches using alkaline or acid-guanidine treatment to eliminate therapeutic antibody interference in the measurement of total target ligand" Journal of Pharmaceutical and Biomedical Analysis 51:1128-1133 (2010).
Zhong et al., "Identification and inhibition of drug target interference in" Journal of Immunological Methods 355:21-28 (2010).
Dai et al., "Development of a method that eliminates false-positive results due to nerve growth factor interference in the assessment of fulranumab immunogenicity" AAPS J. 16(3):464-477 (2014).
Schwickart et al., "Indentification and elimination of target-related matrix interference in a neutralizing anti-drug antibody assay" 403:52-61 (2014).
Sickert et al., "Improvement of drug tolerance in immunogenicity testing by acid treatment on Biacore" J Immunol Methods. 334:29-36 (2008).
Weeraratne et al., "Development of a biosensor-based immunogenicity assay capable of blocking soluble drug target interference" J Immunol Methods 396:44-55 (2013).
Zhong et al., "Drug Target Interference in Immunogenicity Assays: Recommendations and Mitigation Strategics" AAPS J. 19(6):1564-1575 (2017).

* cited by examiner

*Primary Examiner* — Lisa V Cook
(74) *Attorney, Agent, or Firm* — Jonathan P. Aumais

(57) ABSTRACT

Herein is reported a method for determining in a sample the (total, i.e. binding competent) amount of a ligand of a ligand-binding protein (therapeutic) comprising the following steps in the following order: subjecting the sample to an acid treatment, forming in solution a non-covalent complex comprising i) an anti-ligand antibody, ii) the ligand, and iii) labelled ligand-binding protein, by adding anti-ligand antibody and labelled ligand-binding protein to the sample, and determining the amount of the complex and thereby determining the amount of the ligand of the ligand-binding protein.

17 Claims, 8 Drawing Sheets

THREE-STEP ACID DISSOCIATION ENZYME LINKED IMMUNOSORBENT (TADELIS) ASSAY

CROSS-REFERENCE TO RELATED APPLICATIONS

This application is a continuation of International Patent Application No. PCT/EP2016/080887, having an international filing date of Dec. 14, 2016, the entire contents of which are incorporated herein by reference, and which claims benefit under 35 U.S.C. § 119 to European Patent Application No. 15200446.1, filed on Dec. 16, 2015.

FIELD OF THE INVENTION

The current invention is in the field of immunoassays. Herein is reported a three-step acid dissociation enzyme linked immunosorbent assay (TADELIS assay). The method reported herein is for the determination of the amount of a circulating ligand of a ligand-binding protein therapeutic comprising an acid dissociation step and in solution complex formation step.

BACKGROUND OF THE INVENTION

Moxness, M., et al. (Ann. N. Y. Acad. Sci. USA 1005 (2003) 265-268) reported a radioligand binding assays for total and Ig classes of insulin antibodies (IAB). Test and control sera first were acidified to dissociate bound insulin, and charcoal was added to adsorb the serum insulin. After neutralization, the charcoal with bound insulin was removed from the serum by centrifugation. For each assay, insulin-extracted serum samples were incubated with radiolabeled insulin in the presence and absence of high levels of unlabeled insulin to determine nonspecific binding and total binding, respectively.

Patton, A., et al. (J. Immunol. Meth. 304 (2005) 189-195) reported a bridging ELISA that uses a covalently coupled high density antigen surface combined with an acid dissociation step to allow for antibody detection in the presence of antigen in human serum, i.e. without prior removal of excess antigen.

Lee, J. W., et al. (AAPS J. 13 (2011) 99-110) report that the predominant driver of bioanalysis in supporting drug development is the intended use of the data. Reliable methodologies for measurements of mAb and its target ligand (L) in circulation are crucial for the assessment of exposure-response relationships in support of efficacy and safety evaluations, and dose selection. Ligand-binding assays (LBA) are widely used for the analysis of protein biotherapeutics and target ligands (L) to support pharmacokinetics/pharmacodynamics (PK/PD) and safety assessments. For monoclonal antibody drugs (mAb), in particular, which non-covalently bind to L, multiple forms of mAb and L can exist in vivo, including free mAb, free L, and mono- and/or bivalent complexes of mAb and L. Given the complexity of the dynamic binding equilibrium occurring in the body after dosing and multiple sources of perturbation of the equilibrium during bioanalysis, it is clear that ex vivo quantification of the forms of interest (free, bound, or total mAb and L) may differ from the actual ones in vivo. LBA reagents and assay formats can be designed in principle to measure the total or free forms of mAb and L. However, confirmation of the forms being measured under the specified conditions can be technically challenging.

Kelly, M., et al. (AAPS J., 15 (2013) 646-658) report that one area that has been getting increasing attention recently is in the assessment of "free" and "total" analyte and the impact of the assay format on those assessments. The authors provide a critical review of available literature and prospectively explore methods to mitigate the potential impact of anti-drug antibody on PK assay measurement. Furthermore the methods for increasing drug tolerance in ADA (anti-drug antibody) assays could be re-purposed for assessing or increasing ADA tolerance in PK assays, usually with a preparatory step to break up the immune complex and extract the drug. It must be noted that implementation of such challenging manipulations would not be considered routine for late-stage clinical bioanalysis, but would provide valuable information early on in the investigative stage of method development to pharmacokinetics for their interpretation. Ultimately, any extraction process used to help quantitate drug would likely result in a "total" assessment.

Davis, R. A., et al. (J. Pharm. Biomed. Anal. 48 (2008) 897-901) reported a method for quantifying total (free plus bound) biomarker concentration in the presence of high levels of therapeutic MoAb using a single non-competing MoAb in a capture/acid elution format. This assay has the capability to accurately detect and quantitate circulating ng/ml biomarker levels in the presence of 200 µ/ml or more of therapeutic MoAb.

Salimi-Moosavi, H., et al. (J. Pharm. Biomed. Anal. 51 (2010) 1128-1133) reported alkaline and acid/guanidine treatment approaches to dissociate the protein binding and preferentially denature the ThA. The neutralized target proteins can be determined by ELISA. These methods provide reproducible measurements of total target protein without ThA interference. Serum samples, standards and QCs containing target protein and ThA were treated with alkaline buffer (pH>13) containing casein or acid/guanidine buffer (pH<1). Total target proteins for two different ThA systems were successfully measured and interferences were completely eliminated by the treatments. These methods were successfully applied to analysis in pre-clinical serum samples.

In US 2015/226758 methods and kits for detecting the presence of anti-drug antibodies in a sample, and more particularly to methods and kits for detecting anti-drug antibodies in the presence of a drug in the sample are reported.

In US 2012/269728 devices and methods for real time detection of target agents in a sample are reported. These devices utilize tracking technology and selective binding to allow the identification of one or more target agents in a sample, and preferably in a biological sample.

Li, J., et al. reported the detection of low-affinity anti-drug antibodies and improved drug tolerance in immunogenicity testing by Octet<(>R) biolayer interferometry (J. Pharm. Biomed. Anal. 54 (2011) 286-294).

Mikulskis, A., et al. reported about a solution ELISA as a platform of choice for development of robust, drug tolerant immunogenicity assays in support of drug development (J. Immunol. Meth. 365 (2010) 38-49).

Qiu, Z. J., et al., reported a novel homogeneous biotin-digoxigenin based assay for the detection of human anti-therapeutic antibodies in autoimmune serum (J. Immunol. Meth. 362 (2010) 101-111).

Zhong, Z. D., et al. reported the identification and inhibition of drug target interference in immunogenicity assays (J. Immunol. Meth. 355 (2010) 21-28).

SUMMARY OF THE INVENTION

Herein is reported a method for the determination of circulating ligand/target (secreted as soluble form or shedded) of a protein therapeutic using an immunoassay comprising an acid dissociation step and an in solution complex formation step (three-step acid dissociation enzyme linked immunosorbent assay (TADELIS assay)). In the TADELIS assay for the first time an acid dissociation/recombination step has been employed in an immunoassay for the determination of the amount of circulating ligand.

It has been found that with the method as reported herein the drug tolerance of an immunoassay for the determination of circulating ligand/target of a ligand-binding protein can be improved. The method as reported herein addresses the issue of interference between ligand-binding protein present in the sample (e.g. due to administration) and labelled ligand-binding protein added during the immunoassay. Thus, the method as reported herein is suitable for the analysis of samples from pharmacokinetic and/or pharmacodynamic experiments.

Furthermore it has been found that the use of the ligand-binding protein as reagent allows for the selective detection of "ligand-binding protein-specific" ligand concentration. That is, the method as reported herein only determines the amount of the circulating ligand that can actually be bound by the ligand-binding protein. With the method as reported herein e.g. isoforms or modified forms of the ligand will not be included in the determined amount as the ligand-binding protein itself with its binding specificity is included. Further there is no additional effort required to elucidate whether a commercially available or based on different antibodies/clones "biomarker" assay actually determines the active target only. Thus, only the circulating ligand fraction will be detected which actually can be bound by the ligand-binding protein therapeutic.

In the employed acid dissociation step all bound ligand is released, e.g. from ligand/ligand-binding protein complexes. Thus, with the method as reported herein the total amount of ligand-binding protein-specific ligand in a sample is determined.

The in solution incubation (after the acid dissociation step) with excess of labelled ligand-binding protein after pH adjustment shifts the equilibrium to ligand/labelled ligand-binding protein complexes. Thus, the competition between equally affine ligand-binding proteins can be overcome based on the concentration of labelled ligand-binding protein (ratio of ligand-binding protein in the sample to added labelled ligand-binding protein). With this an adjustment of drug tolerance can be made.

Further the label of the labelled ligand-binding protein has to be different from the member of a binding pair (of the anti-ligand antibody) used for immobilization. By this prerequisite it is ensured that lower concentrations of the anti-ligand antibody (compared to the labelled ligand-binding protein) can be used (for example only a small excess compared to the expected amount of ligand in the sample is required). This prevents the saturation of the solid phase by free (i.e. non-complexed) labelled ligand-binding protein. Thus, in the method as reported herein an excess of labelled ligand-binding protein versus ligand present in the sample is used. This excess is smaller than the excess of (immobilized) anti-ligand antibody versus ligand present in the sample.

In one embodiment the concentration of the ligand-binding protein in the non-diluted sample is 150 µg/mL or less. In one embodiment the concentration of the ligand in the sample is between 75 µg/mL and 0.06 µg/mL.

The method as reported herein employs an inverse format compared to generally used immunoassays. The ligand-binding protein itself (in labelled form) is used for the determination of its circulating ligand. This assures a defined readout. Additionally the recovery of the ligand in the TADELIS assay can be expected to be/is directly suitable for quantification.

By the incubation with excess detection reagent in the absence of the capture reagent a higher/improved drug tolerance of the method (assay) as reported herein was achieved.

One aspect as reported herein is a method for determining in a sample the amount of a ligand of a ligand-binding protein (therapeutic/drug) comprising the following steps in the following order:
  subjecting the sample to an acid treatment,
  forming in solution a non-covalent complex comprising
    i) an anti-ligand antibody,
    ii) the ligand, and
    iii) labelled ligand-binding protein, by adding anti-ligand antibody and labelled ligand-binding protein to the sample, and
  determining the amount of the complex,
  and
  thereby determining the amount of the ligand of the ligand-binding protein.

In one embodiment the method comprises the following steps in the following order:
  subjecting the sample to an acid treatment,
  forming in solution a ternary (non-covalent) complex comprising
    i) an anti-ligand antibody,
    ii) the ligand, and
    iii) labelled ligand-binding protein,
    by adding (and incubating) first the labelled ligand-binding protein to the sample to form a binary labelled ligand-binding protein-ligand complex, and by adding (and incubating) after the formation of the binary complex the anti-ligand antibody to the sample to form a ternary labelled ligand-binding protein-ligand-anti-ligand antibody complex, and
  determining the amount of the ternary (non-covalent) complex,
  and
  thereby determining the amount of the ligand of the ligand-binding protein.

In one embodiment the method is for determining the amount of a ligand that can (specifically) be bound by the ligand-binding protein.

In one embodiment the method is for determining in a sample the total amount of a ligand of a ligand-binding protein.

In one embodiment the sample is a plasma sample or a serum sample.

In one embodiment the sample is from an animal. In one embodiment the animal is selected from a human being and an experimental animal. In one embodiment the sample is from an animal to which the ligand-binding protein had been administered prior to obtaining the sample. In one embodiment the sample is from a patient in need of a treatment with the ligand-binding protein to which the ligand-binding protein had been administered prior to obtaining the sample. In no case is the sample re-applied to a living being after the method had been performed therewith.

In one preferred embodiment the sample is not diluted prior to the acid treatment.

In one embodiment the forming of the non-covalent complex is by incubating the acid-treated sample with an excess of labelled ligand-binding protein. In one embodiment the excess is a 5-fold or more excess by weight. In one embodiment the excess is a 10-fold or more excess by weight. In one embodiment the excess is a 5-fold to 1000-fold excess. In one embodiment the excess is a 5-fold to 700-fold excess. In one embodiment the excess is a 25-fold to 700-fold excess. In one embodiment the excess is an about 27-fold excess. In one embodiment the excess is an about 665-fold excess.

In one embodiment the mass ratio of labelled ligand-binding protein employed in the method to ligand-binding protein in the sample is 0.1 or more. In one embodiment the mass ratio of labelled ligand-binding protein employed in the method to ligand-binding protein in the sample is in the range of 0.1 to 300. In one embodiment the mass ratio of labelled ligand-binding protein employed in the method to ligand-binding protein in the sample is in the range of 0.15 to 500. In one preferred embodiment the mass ratio of labelled ligand-binding protein employed in the method to ligand-binding protein in the sample is in the range of 0.2 to 250.

In one embodiment the mass ratio of anti-ligand antibody employed in the method to ligand-binding protein in the sample is 0.05 or more. In one embodiment the mass ratio of anti-ligand antibody employed in the method to ligand-binding protein in the sample is in the range of 0.05 to 1.

In one embodiment the mass ratio of labelled ligand-binding protein to anti-ligand antibody is 2 or more. In one embodiment the mass ratio of labelled ligand-binding protein to anti-ligand antibody is in the range of 2 to 70. In one embodiment the mass ratio of labelled ligand-binding protein to anti-ligand antibody is in the range of 5 to 50. In one embodiment the mass ratio of labelled ligand-binding protein to anti-ligand antibody is in the range of 5 to 25. In one embodiment the mass ratio of labelled ligand-binding protein to anti-ligand antibody is about 8 to 9.

In one embodiment the non-covalent complex is formed by incubating the acid-treated sample firstly with an excess of labelled ligand-binding protein and secondly with the anti-ligand antibody.

In one embodiment the labelled ligand-binding protein is conjugated to a detectable label.

In one embodiment the anti-ligand antibody is conjugated to a first member of a binding pair.

In one embodiment the method comprises after the forming of the non-covalent complex the step of immobilizing the formed non-covalent complex on a solid support. In one preferred embodiment the solid support is conjugated to a second member of a binding pair that can form a complex with the first member of a binding pair conjugated to the anti-ligand antibody of the non-covalent complex.

In one embodiment the anti-ligand antibody is a polyclonal antibody.

In one embodiment the method comprises the following steps in the following order:
  subjecting the sample to an acid treatment,
  incubating the sample with labelled ligand-binding protein, (which is conjugated to a detectable label,)
  incubating the sample with a (polyclonal) anti-ligand antibody, which is conjugated to a first member of a binding pair,
  applying the sample to a solid support conjugated to the second member of the binding pair (so that the non-covalent complex is conjugated/immobilized via the first member of the binding pair to the solid support), and
  determining the amount of a ligand of a ligand-binding protein by determining the amount of solid phase immobilized labelled ligand-binding protein.

In one embodiment the ligand-binding protein is an antibody or antibody fragment or antibody conjugate.

In one embodiment the ligand-binding protein is an exogenous ligand-binding protein.

In one embodiment the ligand is not an antibody.

In one embodiment the first member of the binding pair is biotin and the second member of the binding pair is streptavidin.

In one embodiment the ratio of the added labelled ligand-binding protein and the added anti-ligand antibody is about 8-9:1 based on molecular weight.

In one embodiment the incubation time with the labelled ligand-binding protein is for at least 20 minutes. In one embodiment the incubation time is from (and including) 20 minutes to 120 minutes. In one embodiment the incubation time is from (and including) 40 minutes to 80 minutes. In one embodiment the incubation time is about 60 minutes.

In one embodiment the incubation time with the anti-ligand antibody is at most 60 minutes. In one embodiment the incubation time is from (and including) 10 minutes to 45 minutes. In one embodiment the incubation time is from (and including) 15 minutes to 30 minutes. In one embodiment the incubation time is about 20 minutes.

In one embodiment the ligand is not an antibody, especially not an anti-drug antibody.

In one embodiment the method is performed in the absence of further ligand and/or ligand-binding protein binders, such as e.g. anti-ligand antibodies or anti-ligand-binding protein antibodies.

DETAILED DESCRIPTION OF THE INVENTION

For the analysis of therapeutic antibodies (tmAbs) as well as the respective therapeutic mAb's ligands (tmAb's ligand or short ligand) in samples of in vitro or in vivo origin a respective assay is necessary, especially in early stages of tmAb development. But in early development stages often the required specific binding reagents, such as anti-idiotypic antibodies for the determination of the tmAb or antibodies binding to different epitopes of the ligand for determination of the tmAb's ligand, are seldom available.

Especially the determination of the tmAb's ligand in samples is important as well as demanding. The tmAb binds to its ligand (in vitro and in vivo) and an equilibrium between free tmAb and free ligand, respectively, as well as mono- and di-complexed tmAb (assuming a bivalent monospecific tmAb) is formed. This equilibrium is dynamic, i.e. the change of the concentration of one component taking part in this equilibrium also changes the concentrations of all other components taking part in this equilibrium. For example, ligand concentrations can be used to determine the biologically active tmAb fraction, to elaborate the relationship between tmAb (bound and free) and ligand (bound and free) and to predict/identify the required dose and treatment regimen.

In more detail, in case that a correlation between the binding of the ligand or even the free ligand and the clinical response of the tmAb could be established the binding and capture of the ligand and correspondingly the fraction of free ligand could serve as a potential marker for pharmacokinetic and pharmacodynamic prediction, respectively, and treatment regimen determination/selection. While the fraction of free, i.e. not bound, tmAb correlates to the availability of tmAb for ligand binding (i.e. therapeutic action) and binding capacity of tmAb to its ligand in vivo, the determination of total tmAb can be used to characterize the interaction between tmAb and its ligand.

For full pharmacokinetic evaluation of, e.g., a tmAb knowledge of soluble target concentrations in plasma/serum samples is important. Typically soluble ligand/target is evaluated as potential biomarker. Often the assays are significantly interfered if the drug is present in the sample due to steric hindrance or overlapping epitopes between the drug and the immunoassay reagent. Sometimes there is a variation in soluble target (e.g. splice variants, hetero vs. homodimers). These might be important for biomarker purposes, but for pharmacokinetic evaluation only the target fraction, which can be bound or is bound by the drug, is important.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity.

In certain embodiments, the antibody is a multispecific antibody, e.g. a bispecific antibody. Multispecific antibodies are monoclonal antibodies that have binding specificities for at least two different sites. In certain embodiments, one of the binding specificities is for a first antigen and the other is for a different second antigen. In certain embodiments, bispecific antibodies may bind to two different epitopes of the same antigen. Bispecific antibodies can be prepared as full length antibodies or antibody fragments. In one embodiment the antibody is a bispecific antibody, which specifically binds to a first and a second antigen. In one embodiment the bispecific antibody has i) a first binding specificity that specifically binds to a first antigen or a first epitope on an antigen, and ii) a second binding specificity that specifically binds to a second antigen or a second epitope on the (same) antigen. In one embodiment the second epitope on the same antigen is a non-overlapping epitope.

Multispecific antibodies are described in WO 2009/080251, WO 2009/080252, WO 2009/080253, WO 2009/080254, WO 2010/112193, WO 2010/115589, WO 2010/136172, WO 2010/145792, or WO 2010/145793.

The conjugation of a tracer and/or capture antibody to its conjugation partner can be performed by different methods, such as chemical binding, or binding via a specific binding pair. The term "conjugation partner" as used herein denotes e.g. solid supports, polypeptides, detectable labels, members of specific binding pairs. In one embodiment the conjugation of the capture and/or tracer antibody to its conjugation partner is performed by chemically binding via N-terminal and/or ε-amino groups (lysine), ε-amino groups of different lysines, carboxy-, sulfhydryl-, hydroxyl-, and/or phenolic functional groups of the amino acid backbone of the antibody, and/or sugar alcohol groups of the carbohydrate structure of the antibody. In one embodiment the capture and/or tracer antibody are/is conjugated to its conjugation partner via a specific binding pair. Preferably the capture antibody is conjugated to biotin and immobilization to a solid support is performed via solid support immobilized avidin or streptavidin. Preferably the tracer antibody is conjugated to digoxigenin and linking to the detectable label is performed via an antibody against digoxigenin.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The principles of different immunoassays are described, for example, by Hage, D. S. (Anal. Chem. 71 (1999) 294R-304R). Lu, B., et al. (Analyst 121 (1996) 29R-32R) report the orientated immobilization of antibodies for the use in immunoassays. Avidin-biotin-mediated immunoassays are reported, for example, by Wilchek, M., and Bayer, E. A., in Methods Enzymol. 184 (1990) 467-469.

Polypeptides and monoclonal antibodies and their constant domains contain a number of reactive amino acid side chains for conjugating to a member of a binding pair, such as a polypeptide/protein, a polymer (e.g. PEG, cellulose or polystyrol), or an enzyme. Chemical reactive groups of amino acids are, for example, amino groups (lysins, alpha-amino groups), thiol groups (cystins, cysteines, and methionins), carboxylic acid groups (aspartic acids, glutamic acids), and sugar-alcoholic groups. Such methods are e.g. described by Aslam M., and Dent, A., in "Bioconjugation", MacMillan Ref. Ltd. 1999, pages 50-100.

One of the most common reactive groups of polypeptides and antibodies is the aliphatic ε-amine of the amino acid lysine. In general, nearly all polypeptides and antibodies contain abundant lysine. Lysine amines are reasonably good nucleophiles above pH 8.0 (pKa=9.18) and therefore react easily and cleanly with a variety of reagents to form stable bonds. Amine-reactive reagents react primarily with lysins and the α-amino groups of proteins. Reactive esters, particularly N-hydroxy-succinimide (NHS) esters, are among the most commonly employed reagents for modification of amine groups. The optimum pH for reaction in an aqueous environment is pH 8.0 to 9.0. Isothiocyanates are amine-modification reagents and form thiourea bonds with proteins. They react with protein amines in aqueous solution (optimally at pH 9.0 to 9.5). Aldehydes react under mild aqueous conditions with aliphatic and aromatic amines, hydrazines, and hydrazides to form an imine intermediate (Schiffs base). A Schiffs base can be selectively reduced with mild or strong reducing agents (such as sodium borohydride or sodium cyanoborohydride) to derive a stable alkyl amine bond. Other reagents that have been used to modify amines are acid anhydrides. For example, diethylenetriaminepentaacetic anhydride (DTPA) is a bifunctional chelating agent that contains two amine-reactive anhydride groups. It can react with N-terminal and ε-amine groups of amino acids to form amide linkages. The anhydride rings open to create multivalent, metal-chelating arms able to bind tightly to metals in a coordination complex.

Another common reactive group in polypeptides and antibodies is the thiol residue from the sulfur-containing amino acid cystine and its reduction product cysteine (or half cystine). Cysteine contains a free thiol group, which is more nucleophilic than amines and is generally the most reactive functional group in a protein. Thiols are generally reactive at neutral pH, and therefore can be coupled to other molecules selectively in the presence of amines. Since free sulfhydryl groups are relatively reactive, proteins with these groups often exist with them in their oxidized form as disulfide groups or disulfide bonds. In such proteins, reduction of the disulfide bonds with a reagent such as dithiothreitol (DTT) is required to generate the reactive free thiol. Thiol-reactive reagents are those that will couple to thiol groups on polypeptides, forming thioether-coupled products. These reagents react rapidly at slight acidic to neutral pH and therefore can be reacted selectively in the presence of amine groups. The literature reports the use of several thiolating crosslinking reagents such as Traut's reagent (2-iminothiolane), succinimidyl (acetylthio) acetate (SATA), and sulfosuccinimidyl 6-[3-(2-pyridyldithio) propionamido] hexanoate (Sulfo-LC-SPDP) to provide efficient ways of introducing multiple sulfhydryl groups via reactive amino groups. Haloacetyl derivatives, e.g. iodoacetamides, form thioether bonds and are also reagents for thiol modification. Further useful reagents are maleimides. The reaction of maleimides with thiol-reactive reagents is essentially the same as with iodoacetamides. Maleimides react rapidly at slight acidic to neutral pH.

Another common reactive group in polypeptides and antibodies are carboxylic acids. Polypeptides and antibodies contain carboxylic acid groups at the C-terminal position and within the side chains of aspartic acid and glutamic acid. The relatively low reactivity of carboxylic acids in water usually makes it difficult to use these groups to selectively modify polypeptides and antibodies. When this is done, the carboxylic acid group is usually converted to a reactive ester by the use of a water-soluble carbodiimide and reacted with a nucleophilic reagent such as an amine, hydrazide, or hydrazine. The amine-containing reagent should be weakly basic in order to react selectively with the activated carboxylic acid in the presence of the more highly basic ε-amines of lysine to form a stable amide bond. Protein crosslinking can occur when the pH is raised above 8.0.

Sodium periodate can be used to oxidize the alcohol part of a sugar within a carbohydrate moiety attached to an antibody to an aldehyde. Each aldehyde group can be reacted with an amine, hydrazide, or hydrazine as described for carboxylic acids. Since the carbohydrate moiety is predominantly found on the crystallizable fragment (Fc) region of an antibody, conjugation can be achieved through site-directed modification of the carbohydrate away from the antigen-binding site. A Schiffs base intermediate is formed, which can be reduced to an alkyl amine through the reduction of the intermediate with sodium cyanoborohydride (mild and selective) or sodium borohydride (strong) water-soluble reducing agents.

The term "experimental animal" denotes any mammal including domestic and farm animals as well as higher primates, however, excluding humans. In one embodiment the method as reported herein is performed with a sample obtained from an experimental animal selected from the group comprising mouse, rat, rabbit, goat, sheep, dog, cat, and primates like lemurs, monkeys, marmosets, and apes. If the experimental animal is a lesser ape the closest relatives to mankind, the great apes, especially the group of chimpanzees, bonobos, gorillas and orangutans are excluded.

The term "sample" includes, but is not limited to, any quantity of a substance from a living thing or formerly living thing. Such living things include, but are not limited to, humans, mice, monkeys, rats, rabbits, and other animals. In one embedment the sample is obtained from a monkey, especially a cynomolgus monkey, or a rabbit, or a mouse, or rat, or a human. Such substances include, but are not limited to, in one embodiment whole blood, plasma or serum from an individual, which are the most widely used sources of sample in clinical routine.

The term "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component is distinguished from inert solid surfaces in that a "solid phase" contains at least one moiety on its surface, which is intended to interact with a substance in a sample. A solid phase may be a stationary component, such as a tube, strip, cuvette or microtiter plate, or may be non-stationary components, such as beads and microparticles. A variety of microparticles that allow either non-covalent or covalent attachment of proteins and other substances may be used. Such particles include polymer particles such as polystyrene and poly (methylmethacrylate); gold particles such as gold nanoparticles and gold colloids; and ceramic particles such as silica, glass, and metal oxide particles. See for example Martin, C. R., et al., Analytical Chemistry-News & Features, 70 (1998) 322A-327A, or Butler, J. E., Methods 22 (2000) 4-23.

Chromogens (fluorescent or luminescent groups and dyes), enzymes, NMR-active groups or metal particles, haptens, e.g. digoxigenin, are examples of "detectable labels". The detectable label can also be a photoactivatable crosslinking group, e.g. an azido or an azirine group. Metal chelates which can be detected by electrochemiluminescence are also preferred signal-emitting groups, with particular preference being given to ruthenium chelates, e.g. a ruthenium (bispyridyl)$_3^{2+}$ chelate. Suitable ruthenium labeling groups are described, for example, in EP 0 580 979, WO 90/05301, WO 90/11511, and WO 92/14138. For direct detection the labeling group can be selected from any known detectable marker groups, such as dyes, luminescent labeling groups such as chemiluminescent groups, e.g. acridinium esters or dioxetanes, or fluorescent dyes, e.g. fluorescein, coumarin, rhodamine, oxazine, resorufin, cyanine and derivatives thereof. Other examples of labeling groups are luminescent metal complexes, such as ruthenium or europium complexes, enzymes, e.g. as used for ELISA or for CEDIA (Cloned Enzyme Donor Immunoassay, e.g. EP-A-0 061 888), and radioisotopes.

Indirect detection systems comprise, for example, that the detection reagent, e.g., the detection antibody is labeled with a first partner of a bioaffine binding pair. Examples of suitable binding pairs are hapten or antigen/antibody, biotin or biotin analogues such as aminobiotin, iminobiotin or desthiobiotin/avidin or Streptavidin, sugar/lectin, nucleic acid or nucleic acid analogue/complementary nucleic acid, and receptor/ligand, e.g., steroid hormone receptor/steroid hormone. Preferred first binding pair members comprise hapten, antigen and hormone. Especially preferred are haptens like digoxin and biotin and analogues thereof. The second partner of such binding pair, e.g. an antibody, Streptavidin, etc., usually is labeled to allow for direct detection, e.g., by the labels as mentioned above.

A "protein" is a polymer consisting of amino acids joined by peptide bonds, whether produced naturally or synthetically. Proteins of less than about 20 amino acid residues may be referred to as "peptides", whereas molecules comprising less than 50 amino acid residues may be referred to as "polypeptides". A protein may also comprise non-amino acid components, such as carbohydrate groups, metal ions, or carboxylic acid esters. The non-amino acid components may be added by the cell, in which the protein is expressed, and may vary with the type of cell. Proteins are defined herein in terms of their amino acid backbone structure or the nucleic acid encoding the same. Additions such as carbohydrate groups are generally not specified, but may be present nonetheless.

The term "total amount of a ligand of a ligand-binding protein in a sample" denotes the sum free circulating ligand, i.e. ligand that is not bound to any other component, and bound circulating ligand, i.e. ligand that is bound to any other component in an acid-dissociable form.

The Method as Reported Herein

With the method as reported herein the detection of "drug-specific" target concentration is possible. No additional effort to elucidate whether a "biomarker" assay (commercial or based on different antibodies/clones) detects the same target is necessary. Furthermore the required reagents are available at early project stages and this enables early project support (drug is available, polyclonal antibody is available within moderate timelines). Thus, the method (=TADELIS assay format) as reported herein is universally applicable.

The circulating ligand determined in the method as reported herein is the target of the ligand-binding protein. The ligand-binding protein is a therapeutic protein intended for the use in a human being to treat an illness. Thus, the ligand has a specific function inside a living organism (human or non-human) that is exerted by the binding of the ligand to its endogenous counterpart. Thus, the ligand is able to bind to one or more entities beside the exogenous ligand-binding protein.

Further, the ligand can exist in vivo in different forms, such as e.g. different isoforms, modified form(s), whereof only a limited number, or even a single form, is the target of the ligand-binding protein. Thus, only this/these form/forms should be determined.

Herein is reported a method for the determination of circulating ligand of a ligand-binding protein that can actually be recognized and bound by the ligand-binding protein in vivo. The method is for the determination of the total amount of the circulating binding-competent ligand of a therapeutic ligand-binding protein.

In general the binding of the ligand-binding protein to its ligand, i.e. target, will be a dynamic equilibrium influenced by their respective concentrations as well as the affinity and/or avidity of the ligand-binding protein for the ligand. Thus, for understanding this equilibrium in vivo, i.e. for determining the pharmacokinetic and pharmacodynamic characteristics of the ligand-binding protein, the concentration, i.e. the amount, of both (ligand and ligand-binding protein) in plasma or serum samples have to be determined.

Due to the presence of the ligand-binding protein in vivo the concentration of the ligand can vary/change. Upon binding of the ligand by the ligand-binding protein the ligand is converted to a latently inactive form. This can result in a lowering of the circulating ligand concentration (e.g. if the bound ligand is removed from the circulation together with the ligand-binding protein), an almost constant circulating ligand concentration (e.g. if the production of ligand is increased to counteract the ligand-binding protein induced reduction of the concentration of the ligand), or an increased circulating ligand concentration (e.g. if the production of the ligand is increased or the ligand accumulates or clearance of the ligand is reduced). In the latter case free ligand and total ligand increase after dosing. This may counteract the intended therapeutic effect of the ligand-binding protein or may cause side-reactions.

The total amount of the circulating ligand can be used to characterize the effect of the administered ligand-binding protein in vivo.

The TADELIS assay format as used in the method as reported herein allow for drug tolerance (=ligand-binding protein tolerance).

The TADELIS assay format as used in the method allows an efficient way to detect a ligand-binding protein with enhanced drug tolerance (=ligand-binding protein tolerance).

It has been found that by using the inverse TADELIS assay format the drug tolerance of the method could be increased, i.e. by the modification of the detection reagent to comprise a different conjugation partner as the capture reagent. Thereby the capture reagent can be used at minimal required concentrations to enable/enhance sensitivity. This is not crucial for drug tolerance. Thereby amongst other things a lower reagent consumption as compared to a conventional "ADA-like bridging" format with equally modified capture and detection reagents (e.g. both biotinylated) could be achieved. In addition the TADELIS assay used in the method as reported herein has no reagent competition for the same epitope e.g. as in a one-step format (due to multi-step complex formation).

Further the capture reagent can be a polyclonal antibody. By the binding of the labelled ligand-binding protein to the ligand the respective epitope becomes masked. Due to the polyclonal nature of the capture reagent also other epitopes on the ligand will be recognized and used for formation of the complex. Additionally as the complete formed complex is immobilized no binding sites on the solid support are lost due to steric hindrance by the bound anti-ligand antibody (capture reagent). Thus, the effective loading of the solid surface is increased compared to other assay setups.

In one embodiment (solely) the routinely determined off-rate of the ligand-binding protein is relevant for and can be used to determine the incubation time, e.g. to minimize the competition of capture reagent and detection reagent for the same epitope. The binding characteristics of the capture reagent in case a polyclonal antibody is used (epitope distribution, affinities) are not relevant and do not have to be determined. This allows the use of polyclonal capture reagents from different sources or different charges without affecting the drug tolerance of the assay (increased assay robustness).

The method as reported herein will be exemplified in the following. Therefore specific reagents have to be used. But this has not to be construed as limitation of the method as reported herein. It is a mere exemplification. The real scope of the invention is set up in the claims.

Components used for performing the examples:
ligand-binding protein: anti-mesothelin antibody conjugated to *pseudomonas* exotoxin
anti-ligand antibody: polyclonal anti-mesothelin antibody
The TADELIS assay was performed with the steps of:
acid dissociation (10 µL sample; 50 µL 0.1 mol/L glycine solution, pH 2; 30 min)
addition of 50 µL Tris/LowCross-Buffer® comprising a monoclonal anti-mesothelin antibody conjugated to digoxygenin and incubation for one hour
addition to the wells of the multi well plate and incubation for one hour addition of 200 µL LowCross-Buffer® comprising a polyclonal anti-mesothelin antibody preparation conjugated to biotin and incubation for 20 min.

addition of the solution to the wells of a streptavidin coated multi well plate and incubation for 30 min.

removing the supernatant and washing of the wells adding a solution comprising an anti-digoxygenin antibody conjugate to HRP (50 mU)

incubating the plate for 40 min.

removing the supernatant and washing the wells adding substrate solution for the generation of the readout incubating the plate determination of absorption values determining the analyte concentration using the calibration curve.

The assay has been performed using rabbit plasma, which does not contain cross-reactive mesothelin. A calibration curve was generated (shown in FIG. 6). The assay range is of from 0.16 nM to 25 nM (plasma concentration).

The recovery in an assay is defined as the ratio of detected drug to residual drug as shown in the following formula:

$$\text{recovery} = \frac{\text{detected amount of drug}}{(\text{detected amount of drug} + \text{residual amount of drug})}$$

The recovery of the assay can be improved starting from the recovery obtained at a first concentration of the capture antibody or tracer antibody by keeping the concentration of the capture antibody constant and varying the concentration of the tracer antibody (and thereby the ratio) or likewise by keeping the concentration of the tracer antibody constant and varying the concentration of the capture antibody.

With a weight ratio of detection antibody to capture antibody of about 1.7 the average target recovery in this assay is about 24% at a drug concentration of 75 µg/mL, about 56% at a drug concentration of 15 µg/mL, about 86% at a drug concentration of 3 µg/mL, and about 92% at a drug concentration of 0.6 µg/mL.

In a second example with increased ratio also a calibration curve was generated (shown in FIG. 7). The assay range is of from 0.78 nM to 50 nM.

With a weight ratio of detection antibody to capture antibody of about 8.86 the average target recovery in this assay is about 67% at a drug concentration of 75 µg/mL, about 82% at a drug concentration of 15 µg/mL, about 88% at a drug concentration of 3 µg/mL, and about 98% at a drug concentration of 0.6 µg/mL.

In a third example with further increased ratio also a calibration curve was generated (shown in FIG. 8). The assay range is of from 1.56 nM to 50 nM.

With a weight ratio of detection antibody to capture antibody of about 44.3 the average target recovery in this assay is about 83% at a drug concentration of 75 µg/mL, about 83% at a drug concentration of 15 µg/mL, about 86% at a drug concentration of 3 µg/mL, and about 90% at a drug concentration of 0.6 µg/mL.

Even though a recovery of 80% or more is the target for using the assay as reported herein in the analysis of drug-containing samples, e.g. in pre-clinical or clinical trials, it is not mandatory. Nevertheless the data presented above clearly shows that independent of the detection antibody to capture antibody weight ratio a working range with a recovery rate of 80% or more can be identified, i.e. exists. This working range can easily be determined by a person skilled in the art without undue burden, e.g. by performing the analysis of a series of samples with decreasing amount of ligand (=analyte) spiked therein (i.e. present in the sample).

Additionally the assay as reported herein can be performed with any recovery if the results shall be a "yes" or "no", i.e. ligand of the ligand-binding protein (therapeutic) is present or not. In this case the assay has simply to be operated above the limit of detection.

Furthermore, the assay as reported herein has to be validated, like any other assay used for the quantification of an analyte. During this validation the respective working range based on the target recovery will be determined.

Additionally, a calibration curve for the assay as reported herein can be established. With this calibration curve a relation between amount of analyte present in the sample and recovered amount of analyte is established. With this relation any recovery is corrected during the assay result calculation and thereby a low recovery rate is addressed.

Thus, in one embodiment the method as reported herein comprises the step of a)
  subjecting the sample to an acid treatment,
  forming in solution a non-covalent complex comprising
  i) an anti-ligand antibody,
  ii) the ligand, and
  iii) labelled ligand-binding protein,
  by adding anti-ligand antibody and labelled ligand-binding protein to the sample, and
  determining the amount of the complex, b)
  determining a calibration curve by performing step a) with at least two samples obtained by spiking defined but different amounts of the ligand into a ligand-free sample (i.e. comprising the ligand at an amount below the detection limit of step a)), c)
  determining the amount of the ligand of the ligand-binding protein with the result of step a) and of step b).

Thus, in one embodiment the method as reported herein is performed with a weight ratio of detection antibody to capture antibody of about 1.7 at a drug concentration of 5 µg/mL or lower, in one embodiment in the range of 5 µg/mL to 0.01 µg/mL, in a further embodiment in the range of 3 µg/mL to 0.6 µg/mL, and/or with a weight ratio of detection antibody to capture antibody of about 8.85 at a drug concentration of 18 µg/mL or lower, in one embodiment in the range of 18 µg/mL to 0.01 µg/mL, in a further embodiment in the range of 15 µg/mL to 0.6 µg/mL, and/or with a weight ratio of detection antibody to capture antibody of about 44 at a drug concentration of 80 µg/mL or lower, in one embodiment in the range of 80 µg/mL to 0.01 µg/mL, in a further embodiment in the range of 75 µg/mL to 0.6 µg/mL.

Thus, in one embodiment the method as reported herein is performed with a weight ratio of detection antibody to capture antibody of about 1.7 with a detection antibody concentration of about 14 nM at a drug concentration of 5 µg/mL or lower, in one embodiment in the range of 5 µg/mL to 0.01 µg/mL, in a further embodiment in the range of 3 µg/mL to 0.6 µg/mL, and/or with a weight ratio of detection antibody to capture antibody of about 8.85 at a drug concentration of 18

µg/mL or lower, in one embodiment in the range of 18 µg/mL to 0.01 µg/mL, in a further embodiment in the range of 15 µg/mL to 0.6 µg/mL, and/or with a weight ratio of detection antibody to capture antibody of about 44 with a detection antibody concentration of about 338 nM at a drug concentration of 80 µg/mL or lower, in one embodiment in the range of 80 µg/mL to 0.01 µg/mL, in a further embodiment in the range of 75 µg/mL to 0.6 µg/mL.

Assuming a serum concentration of the ligand-binding protein between 10 µg/ml and 150 µg/mL the ratios as listed in the following table are generally employed in the TADELIS assay.

| | | ligand-binding protein concentration in the sample | | |
|---|---|---|---|---|
| | | 150 µg/ml | 75 µg/ml | 10 µg/ml |
| weight ratio to detection reagent | low | 0.15 | 0.3 | 2.3 |
| | medium | 1.87 | 3.74 | 28.1 |
| | high | 2.68 | 5.36 | 40.2 |
| weight ratio to capture reagent | | 0.06 | 0.12 | 0.9 |

Thus, in one embodiment the method as reported herein is performed with a weight ratio of the ligand-binding protein in the sample to the detection antibody of from 0.1 to 45 at a ligand-binding protein concentration in the sample of 150 µg/mL or lower, in one embodiment in the range of 150 µg/mL to 10 ng/mL.

Thus, in one embodiment the method as reported herein is performed with a weight ratio of the ligand-binding protein in the sample to the detection antibody of from 1.75 to 45 at a ligand-binding protein concentration in the sample of 150 µg/mL or lower, in one embodiment in the range of 150 µg/mL to 10 µg/mL.

Thus, in one embodiment the method as reported herein is performed with a weight ratio of the ligand-binding protein in the sample to the detection antibody of from 2.5 to 45 at a ligand-binding protein concentration in the sample of 150 µg/mL or lower, in one embodiment in the range of 150 µg/mL to 10 ng/mL.

Thus, in one embodiment the method as reported herein is performed with a weight ratio of the ligand-binding protein in the sample to the capture antibody of from 0.05 to 0.15 at a ligand-binding protein concentration in the sample of 150 µg/mL or lower, in one embodiment in the range of 150 µg/mL to 10 µg/mL.

The TADELIS assay has a total runtime of about 3.5 hours.

Comparative Assay Formats

In the following three different generally known assay formats have been adapted to the TADELIS assay as far as possible. Especially the hitherto unreported use of an acid dissociation step in a ligand detection assay has been included in these assays.

1. Commercial Mesothelin Assay

The commercially available mesothelin assay Mesomark® from the company Fujirebio Diagnostics, Inc. (Malvern, Pa., USA) was performed according to the manufacturer's instructions.

The Mesomark® assay is a manual enzyme-linked immunosorbent assay for the quantitative measurement of soluble mesothelin-related peptides (SMRP). SMRP is a biomarker that is released into the bloodstream by mesothelioma cells. A blood sample is taken from the patient and then tested to determine the level of SMRP present in the blood. The determination of the amount of SMRP present in the blood is made by using monoclonal antibodies known to specifically bind to SMRP. By measuring the amount of bound antibodies, the amount of SMRP present in the patient's blood can be calculated (information taken from the website of the manufacturer).

The detection is done by a colorimetric reaction using a standard ELISA microplate sandwich assay. Two different monoclonal antibodies are used: one for the capture of the SMRP molecules and one for the detection of the SMRP molecules. The colorimetric reaction is by addition of chromogenic substrate reacting with a horseradish peroxidase (HRP) labelled antibody.

The assay comprises the steps of:
dilution of the serum sample (1:101, 10 µL sample and 1 mL buffer)
adding the diluted sample (100 µL) to the wells of a micro titer plate coated with the capture monoclonal antibody
incubating the plate with shaking (700 rpm) for about 60 minutes at room temperature
removing the supernatant and thoroughly washing the wells
adding 100 µL of a solution comprising the second monoclonal antibody conjugate to HRP
incubating the plate with shaking (700 rpm) for about 60 minutes at room temperature
removing the supernatant and thoroughly washing the wells
adding 100 µL of the substrate solution for the generation of the readout
incubating the plate with shaking (700 rpm) for about 15 minutes at room temperature
stopping the reaction by the addition of hydrochloric acid (100 µL, 1% (w/v))
determination of absorption values
determining the analyte concentration using the calibration curve.

The assay has been performed using rabbit serum, using the calibration probes and quality control samples of the kit. Although rabbit serum contains rabbit mesothelin this is not cross-reactive in this assay as the provided antibodies do not bind to rabbit mesothelin. Therefore only samples with spiked human mesothelin can be determined.

A calibration curve spanning the concentrations of 0 nM to 32 nM of mesothelin was generated (shown in FIG. 3). The assay range is of from 2 nM to 32 nM.

The target recovery in this assay is between 96% and 104%, on average about 100% for the calibration samples. With quality control samples the recovery is between 93% and 96%.

The Mesomark® assay has a total runtime of about 2.5 hours. This assay does not detect cynomolgus mesothelin.

2. ADA Format

In this comparative example the same reagent as for the TADELIS assay have been used.

The assay comprises the steps of:
acid dissociation (10 µL sample; 50 µL 0.1 mol/L glycine solution, pH 2; 30 min.)
addition of 50 µL Tris/LowCross-Buffer® (2100 µL LowCross-Buffer® plus 900 µL 0.5 M Tris-HCl (pH 8.5)) comprising two antibody solutions (mAb and pAb) binding to different epitopes of the target one conjugated to biotin and one conjugated to digoxigenin and 200 µL LowCross-Buffer® to the acid dissociation and incubation for one hour addition to the wells of the streptavidin coated multi well plate and incubation for one hour removing the supernatant and washing of the wells adding a solution comprising an anti-digoxygenin antibody conjugate to HRP (50 mU)

incubating the plate for about one hour removing the supernatant and washing the wells adding substrate solution for the generation of the readout incubating the plate determination of absorption values or fluorescence units determining the analyte concentration using the calibration curve.

The assay has been performed using rabbit plasma, which does not contain cross-reactive mesothelin. A calibration curve was generated (shown in FIG. 5). The assay range is of from 0.78 nM to 50 nM.

The average target recovery in this assay is about 54% at a drug concentration of 75 µg/mL, about 80% at a drug concentration of 15 µg/mL, about 91% at a drug concentration of 3 µg/mL, and about 98% at a drug concentration of 0.6 µg/mL.

The ADA format assay has a total runtime of about 4 hours.

The ADA format requires normally at least two monoclonal antibodies of binding to different epitopes on the target but with the same species cross-reactivity. It is questionable if two antibodies binding to non-interfering epitopes have the same species cross-reactivity/affinity can be provided.

3. Serial Mesothelin Assay

In this comparative example the same reagent as for the TADELIS assay have been used.

The assay comprises the steps of:
the wells of a streptavidin coated multi well plate were incubated with biotin labelled polyclonal anti-mesothelin antibody (500 ng/mL; 1.25 h)

removing the supernatant and washing of the wells acid dissociation (10 µL sample; 50 µL 0.1 mol/L glycine solution, pH 2; 30 min.)

addition of 50 µL Tris/LowCross-Buffer® (2100 µL LowCross-Buffer® plus 900 µL 0.5 M Tris-HCl (pH 8.5)) and 200 µL LowCross-Buffer® to the acid dissociation and addition to the wells of the multi well plate and incubation for one hour removing the supernatant and washing of the wells addition of a solution comprising digoxigenin-labelled monoclonal anti-mesothelin antibody (500 ng/mL) and incubation for one hour removing the supernatant and washing of the wells adding a solution comprising an anti-digoxygenin antibody conjugate to HRP (50 mU)

incubating the plate for about one hour removing the supernatant and washing the wells adding substrate solution for the generation of the readout incubating the plate determination of absorption values determining the analyte concentration using the calibration curve.

The assay has been performed using rabbit plasma, which does not contain cross-reactive mesothelin. A calibration curve spanning the concentrations of 0 nM to 25 nM of mesothelin was generated (shown in FIG. 4). The assay range is of from 0.39 nM to 25 nM.

The average target recovery in this assay is about 20% at a drug concentration of 9 µg/mL, about 44% at a drug concentration of 3 µg/mL, and about 71% at a drug concentration of 1 µg/mL.

The assay has been re-performed with a 5-times increased a ratio of detection antibody to capture antibody. The average target recovery in this case is about 10% at a drug concentration of 75 µg/mL, about 12% at a drug concentration of 15 µg/mL, about 34% at a drug concentration of 3 µg/mL, and about 69% at a drug concentration of 0.6 µg/mL.

The serial assay has a total runtime of about 5 hours.

SUMMARY

As can be seen from the table below the TADELIS assay as reported herein has advantages with respect to early (in project life time) availability of employed reagents, mean recovery of samples containing drug, covered species range and time with respect to other assay formats.

| assay format | species cross reactivity | clonality | | mean recovery of drug containing samples | mean recovery of 75 µg/mL drug containing samples | assay time |
| --- | --- | --- | --- | --- | --- | --- |
| | | capture reagent | detection reagent | | | |
| Mesomark® | no | monoclonal | monoclonal | cynomolgus mesothelin is not detectable | — | ≈2.5 h |
| ADA format | maybe | monoclonal/ polyclonal | monoclonal | ≈80% | ≈54% | ≈4 h |
| serial assay | yes | polyclonal | monoclonal | ≈30% | ≈10% | ≈5 h |
| TADELIS assay | yes | polyclonal | monoclonal | ≈85% | ≈83% | ≈3.5 h |

The following examples and figures are provided to aid the understanding of the present invention, the true scope of which is set forth in the appended claims. It is understood that modifications can be made in the procedures set forth without departing from the spirit of the invention.

EXAMPLE 1

Method as Reported Herein

Figure 1:
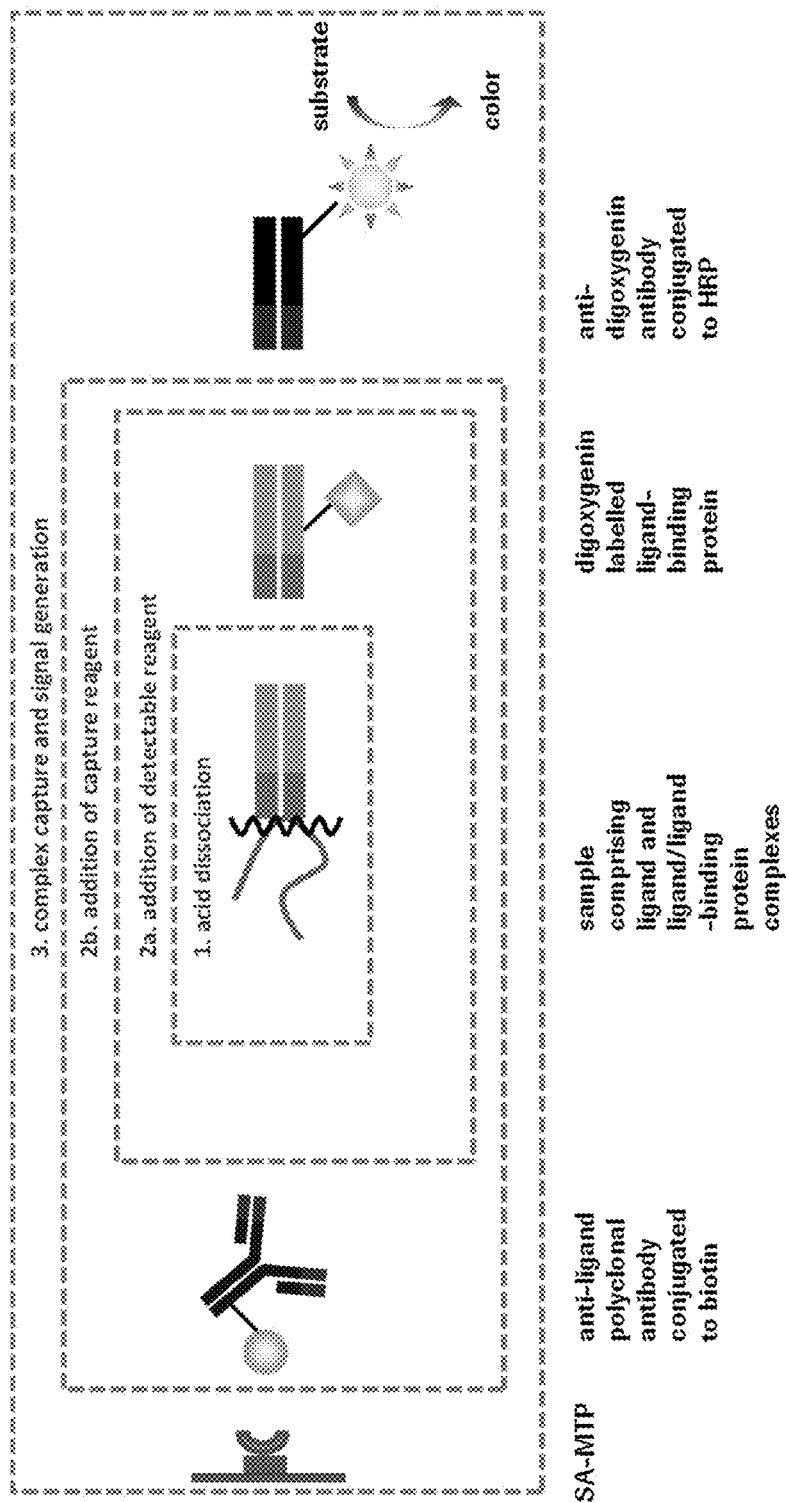
FIG. 1 Overall scheme of the method as reported herein exemplified with the compounds used in Example 1.
Figure 2:
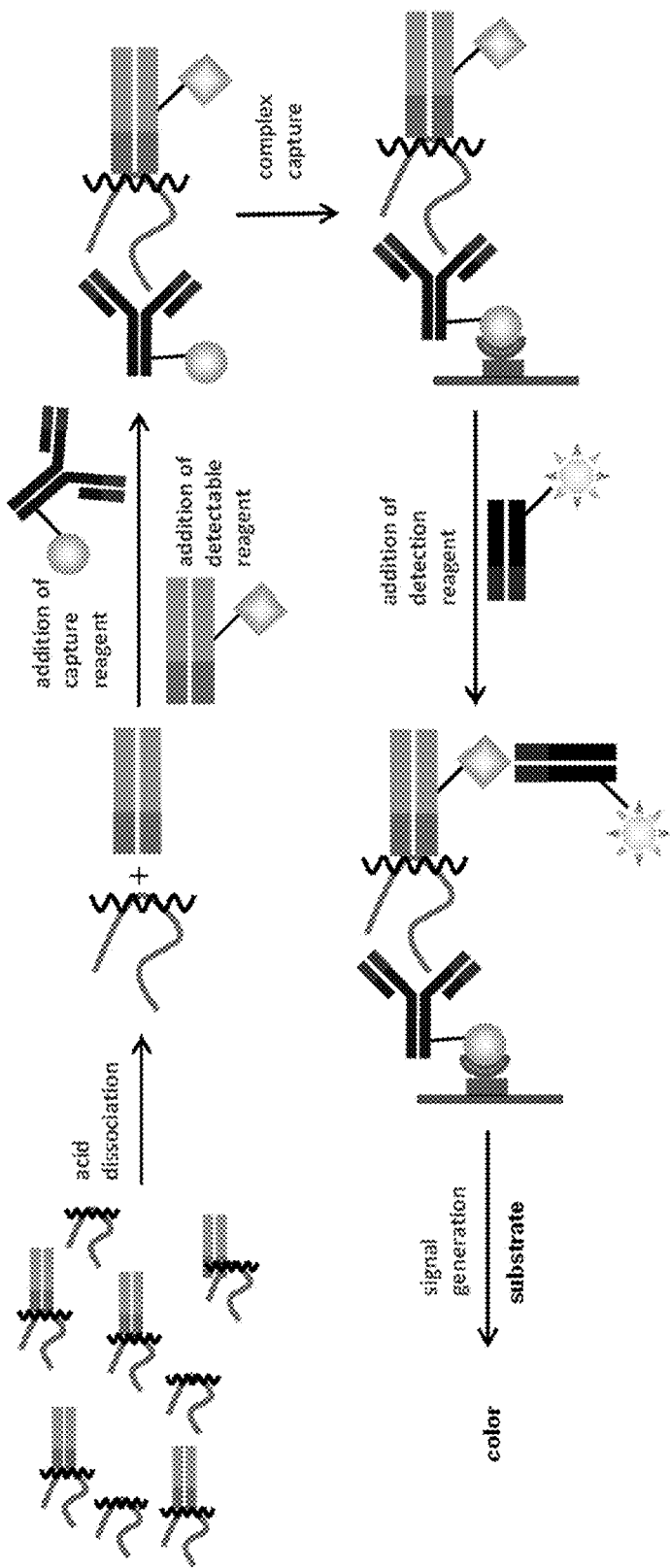
FIG. 2 Flow-chart of the method as reported herein exemplified with the compounds used in Example 1.
Figure 3:
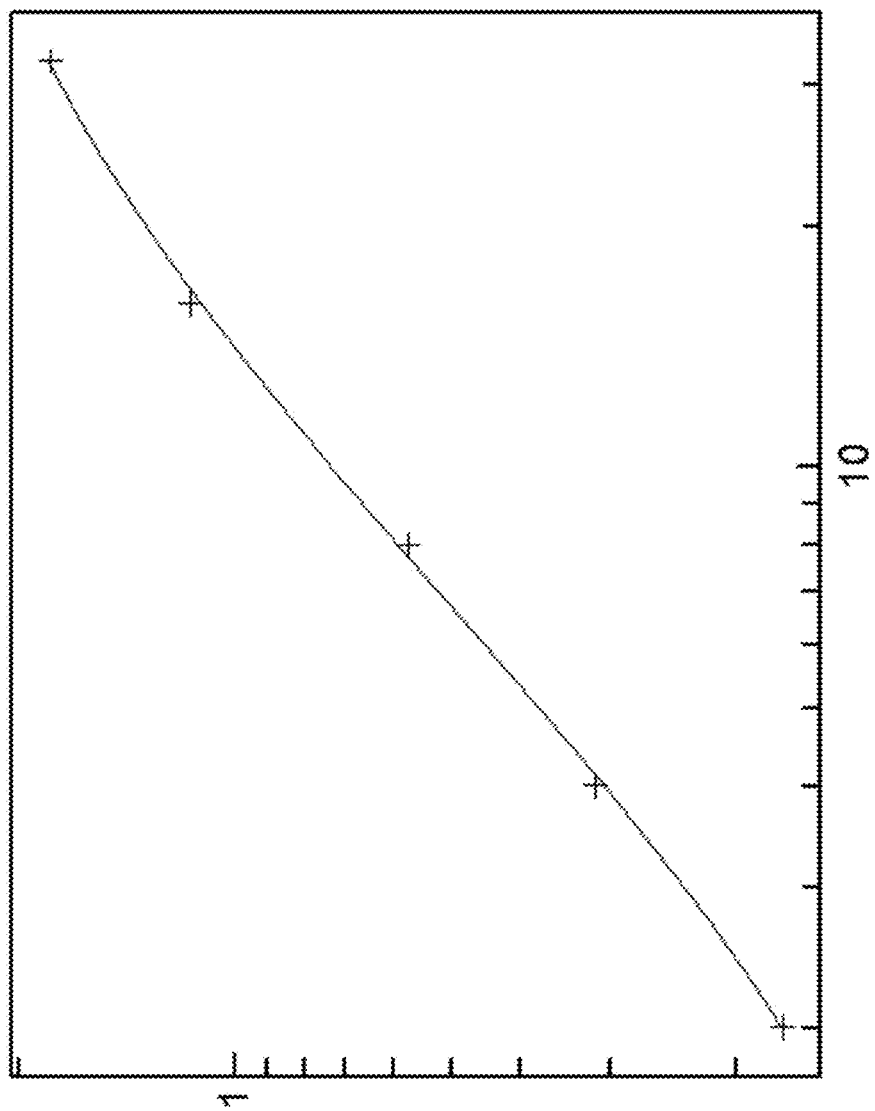
FIG. 3 Mesomark® assay calibration curve (x-axis: target concentration; y-axis: optical density).
Figure 4:
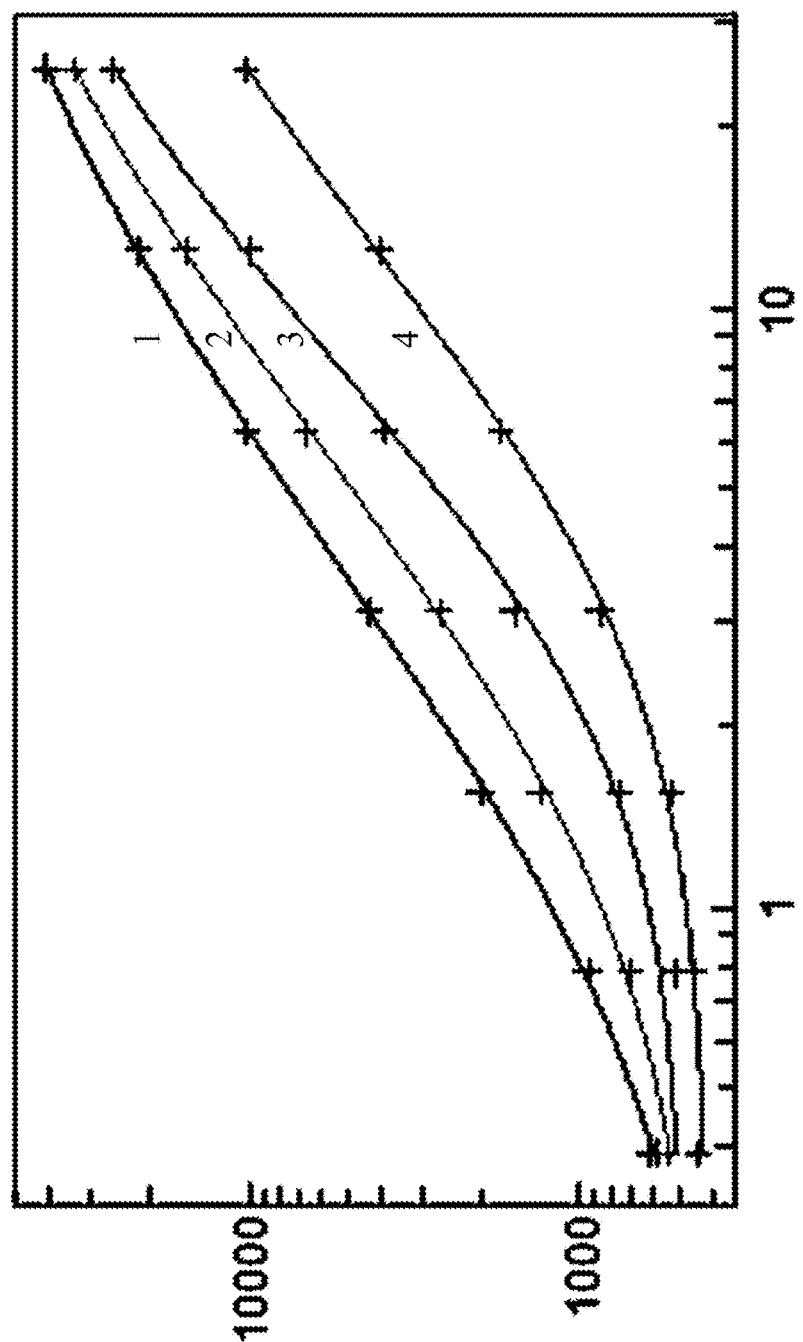
FIG. 4 Drug tolerance of serial mesothelin assay (x-axis: target concentration; y-axis: [FU]); 1: no drug; 2: 1 ng/mL drug; 2: 3 ng/mL drug; 4: 9 ng/mL drug.
Figure 5:
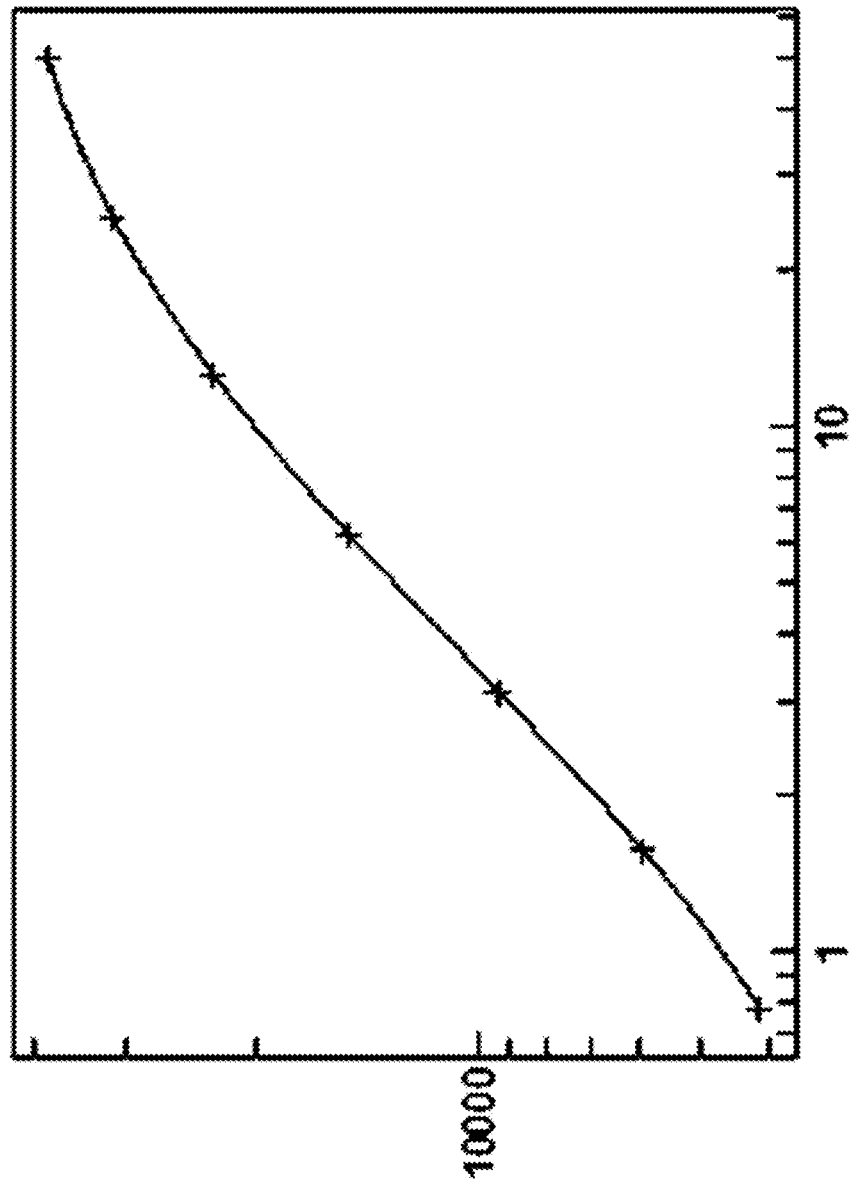
FIG. 5 ADA format assay calibration curve (x-axis: target concentration; y-axis: optical density).
Figure 6:
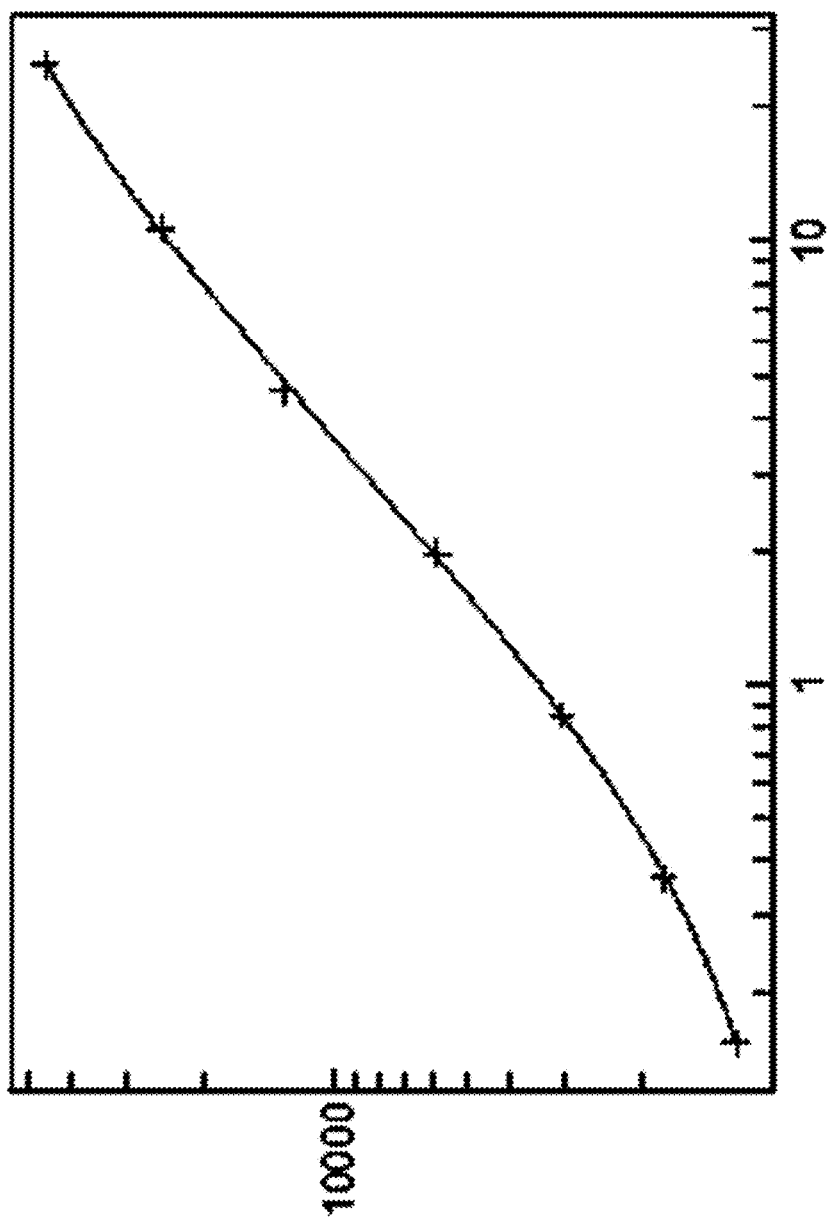
FIG. 6 TADELIS format assay calibration curve (x-axis: target concentration; y-axis: optical density) at a weight ratio of detection antibody to capture antibody of about 1.7.
Figure 7:
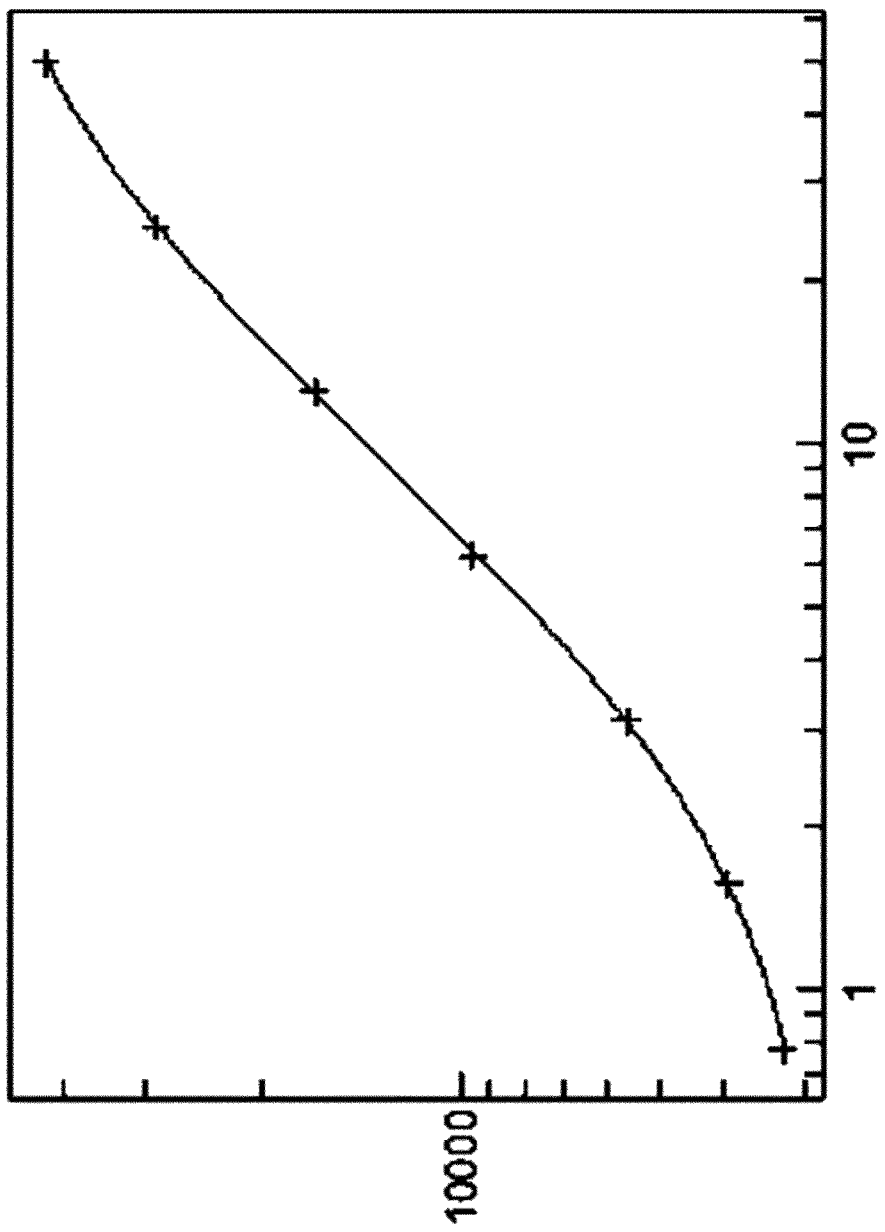
FIG. 7 TADELIS format assay calibration curve (x-axis: target concentration; y-axis: optical density) at a weight ratio of detection antibody to capture antibody of about 8.86.
Figure 8:
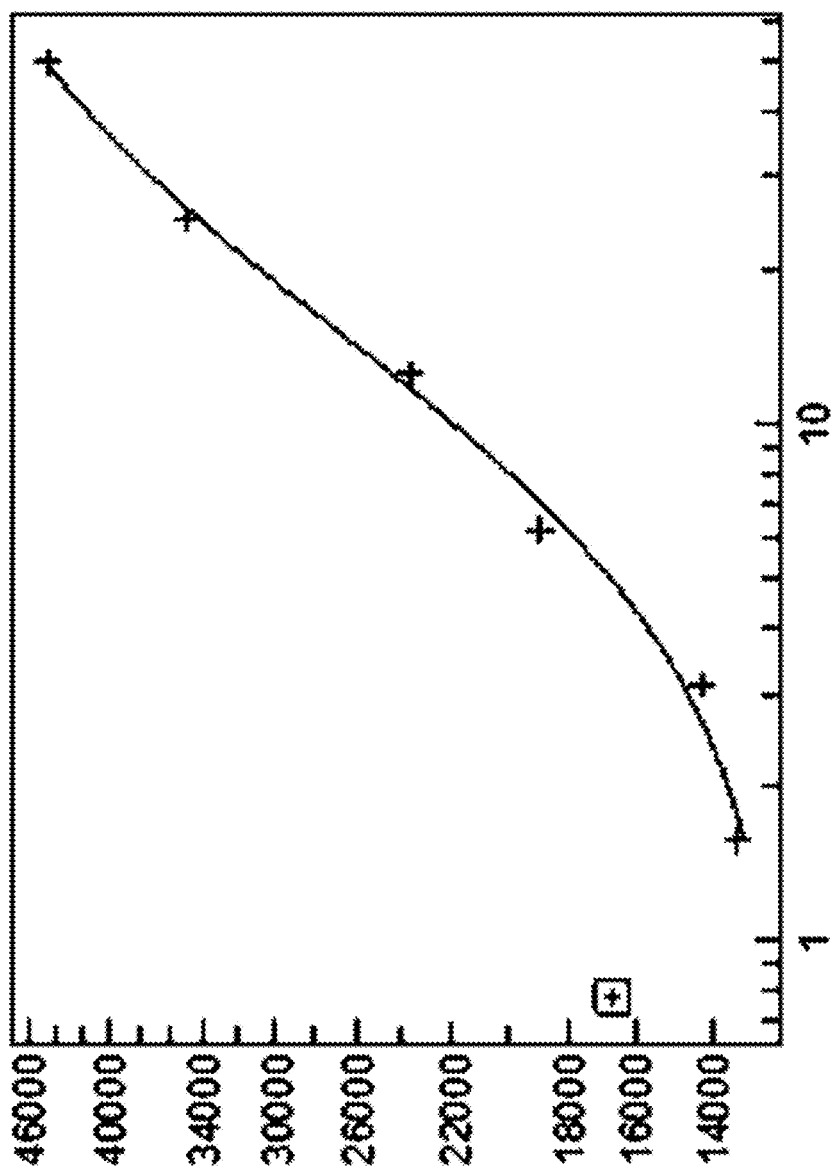
FIG. 8 TADELIS format assay calibration curve (x-axis: target concentration; y-axis: optical density) at a weight ratio of detection antibody to capture antibody of about 44.3.

Positive control standards were prepared in 100% rabbit pooled plasma using human mesothelin to construct a calibration curve in the concentration range from 50 nM to 0 nM (50.0 nM, 21.45 nM, 9.21 nM, 3.95 nM, 1.70 nM, 0.73 nM, 0.31 nM and 0 nM). The final calibrator concentrations were achieved by a dilution of one to one with rabbit pooled plasma (dilution factor=2). Additional quality control samples were prepared in 100% rabbit pooled plasma (separate dilution) with the following concentrations: 25, 17.5, 12.5, 0.469 and 0.156 nM.

Positive test samples were prepared by a one to one dilution (dilution factor=2) of rabbit pooled plasma containing 150, 30, 6 and 1.2 µg/mL drug.

10 µL of test samples, quality control samples, blank sample and each positive control standard were mixed with 50 µl 0.1 M glycine-HCl (pH 2.0) solution for 30 min. The mixture was thereafter neutralized by adding 50 µL of the DIG-conjugated detection reagent (2,100 µL LowCross® buffer containing DIG-conjugated detection reagent (c=4.5 µg/mL) and 900 µL 0.5 M Tris buffer (pH=8.5)). The neutralized sample was incubated for 60 min. An extension of the immune complex was enabled by adding 200 µL of biotinylated capture reagent (biotinylated polyclonal anti-human mesothelin antibody) with a concentration of 450 ng/mL and incubated for 20 min. The total sample volume is 310 µL containing 3.2% plasma.

100 µl of each sample were added in duplicate to a streptavidin coated microtiter plate and incubated for 30 min. on a microtiter plate shaker. The plate is washed three times with phosphate-buffered saline solution containing 0.05% Tween-20. 100 µL anti-digoxigenin antibody Fab fragments conjugated to horseradish peroxidase (HRP) (poly) with a final concentration of 50 mU/mL was added to each well and incubated for 40 min. The plate was washed thereafter three times with phosphate-buffered saline solution containing 0.05% Tween20.

150 µL HPPA (3-(4-hydroxyphenyl) propionic acid solution (83 mg HPPA in 25 mL 0.1 Tris buffer pH=8.5 supplemented with 3.75 µL 30% H2O2) was added to each well and light emission was determined at an emissions wavelength of 405 nm (excitation wavelength of 320 nm).

A standard calibration curve was generated by a non-linear 4 parameter fit using a Wiemer-Rodbard function. The measurement was defined to be acceptable if the recovery of the quality control samples are within 20% of the nominal concentration. In this experiment the recovery was in the range of 83% to 108%.

What is claimed is:

1. A method for determining in a sample the total amount of a ligand of a ligand-binding protein therapeutic comprising the following steps in the following order:
   subjecting the sample to an acid treatment,
   forming in solution a ternary complex comprising
   i) an anti-ligand antibody,
   ii) the ligand, and
   iii) labelled ligand-binding protein,
   by adding first the labelled ligand-binding protein to the sample to form a binary labelled ligand-binding protein-ligand complex, and by adding after the formation of the binary complex the anti-ligand antibody to the sample to form a ternary labelled ligand-binding protein-ligand-anti-ligand antibody complex, and
   determining the amount of the ternary complex,
   and
   thereby determining the amount of the ligand of the ligand-binding protein.

2. The method according to claim 1, wherein the method is for determining the amount of a ligand that can specifically be bound by the ligand-binding protein.

3. The method according to claim 1, wherein the sample is a plasma sample or a serum sample.

4. The method according to claim 1, wherein the sample is not diluted prior to the acid treatment.

5. The method according to claim 1, wherein the forming of the complex is by incubating the acid-treated sample with an excess of labelled ligand-binding protein.

6. The method according to claim 1, wherein the forming of the complex is by incubating the acid-treated sample firstly with an excess of labelled ligand-binding protein and secondly with the anti-ligand antibody.

7. The method according to claim 1, wherein in the forming of the complex the labelled ligand-binding protein is conjugated to a detectable label.

8. The method according to claim 1, wherein the anti-ligand antibody is conjugated to a first member of a binding pair.

9. The method according to claim 1, wherein the method comprises after the forming of the ternary complex the step of immobilizing the formed ternary complex on a solid support.

10. The method according to claim 9, wherein the solid support is conjugated to the second member of the binding pair that can form a complex with the first member of the binding pair conjugated to the anti-ligand antibody.

11. The method according to claim 1, wherein the anti-ligand antibody is a polyclonal antibody.

12. The method according to claim 1, wherein the method comprises the following steps in the following order:
   subjecting the sample to an acid treatment,
   incubating the sample with labelled ligand-binding protein, which is conjugated to a detectable label,
   incubating the sample with a polyclonal anti-ligand antibody, which is conjugated to a first member of a binding pair,
   applying the sample to a solid support conjugated to a second member of the binding pair that forms with the first member of the binding pair a non-covalent complex, and
   determining the amount of a ligand of a ligand-binding protein by determining the amount of solid phase immobilized labelled ligand binding protein.

13. The method according to claim 1, wherein the ligand-binding protein is an antibody.

14. The method according to claim 8, wherein the first member of the binding pair is biotin.

15. The method according to claim 1, wherein the ratio of the added labelled ligand binding protein and the added anti-ligand antibody is 8-9:1 based on molecular weight.

16. The method according to claim 1, wherein the ternary complex is a non-covalent complex.

17. The method according to claim 10, wherein the second member of the binding pair is streptavidin.

* * * * *